United States Patent [19]

De Haan et al.

[11] Patent Number: 5,962,510
[45] Date of Patent: Oct. 5, 1999

[54] ANTIFUNGAL COMPOSITION

[75] Inventors: Ben Rudolf De Haan, Voorburg; Jacobus Stark, Rotterdam, both of Netherlands; Vincenzo Bozzetti, Casteldidone, Italy

[73] Assignee: Gist-brocades B.V., Netherlands

[21] Appl. No.: 09/044,069

[22] Filed: Mar. 18, 1998

[30] Foreign Application Priority Data

Mar. 18, 1997 [EP] European Pat. Off. ............. 97200804
Nov. 25, 1997 [EP] European Pat. Off. ............. 97203693

[51] Int. Cl.$^6$ ............................ A01N 43/02; A01N 43/16
[52] U.S. Cl. ............................... 514/450; 514/460
[58] Field of Search ..................... 424/439, 442; 514/937, 450, 400

[56] References Cited

U.S. PATENT DOCUMENTS

| | | | |
|---|---|---|---|
| 4,238,475 | 12/1980 | Witzel | 424/48 |
| 4,542,020 | 9/1985 | Jackson | 514/31 |
| 4,661,023 | 4/1987 | Hilfiker | 405/262 |
| 4,681,302 | 7/1987 | Thompson | 256/13.1 |
| 4,728,227 | 3/1988 | Wilson et al. | 405/284 |
| 4,826,822 | 5/1989 | Anderson | 514/31 |
| 5,044,834 | 9/1991 | Janopaul, Jr. | 405/284 |
| 5,292,532 | 3/1994 | Bombart | 424/405 |
| 5,435,669 | 7/1995 | Weber | 405/284 |
| 5,552,151 | 9/1996 | Noordam et al. | 424/439 |

FOREIGN PATENT DOCUMENTS

| | | |
|---|---|---|
| 0 513 922 | 11/1992 | European Pat. Off. . |
| 0 678 241 | 10/1995 | European Pat. Off. . |
| 1 122 005 | 7/1968 | United Kingdom . |
| 2 155 330 | 9/1985 | United Kingdom . |

OTHER PUBLICATIONS

H. Toolens: "A selective medium for the detection of Brevibacterium linens in cheese", vol. 25, No. 2, 1970, Muchen De, pp. 79–83.

Holley R A:"Prevention of Surface Mold Growth on Italian Dry Sausage by Natamycin and Potassium Sorbate", Applied and Environment Microbiology, vol. 41, No. 2, Feb. 1981, pp. 422–429.

P.M. Scott, "Mycotoxigenic Fungal Contaminants of Cheese and other Dairy Products", Mycotoxins in Dairy Products, Chapter 7, pp. 193–259.

H.A. Morris, "Control of Surface Growth on Blue Cheese Using Pimaricin", Cultured Dairy Products Journal, May 1980, pp. 21–23.

P.C. Moerman, "Schimmelwering op vieeswaren door Pimaricine", Voedingsmiddelentechnologies 3 (1972), pp. 261–264.

C.B.G. Daamen en G. van den Berg, "Voorkoming van schimmelgroei op de korst van kaas met behulp van natamycine", Voedingsmiddelentechnologie,Jan. 24 (1985) pp. 26–29.

*Primary Examiner*—Jose' G. Dees
*Assistant Examiner*—Alton Pryor
*Attorney, Agent, or Firm*—Morrison & Foerster LLP

[57] ABSTRACT

An aqueous composition is disclosed which comprises 0.1 to 20 g/l of polyene fungicide, 0.5 to 50 g/l of a suitable thickener and optionally 20 to 250 g/l of salt.

13 Claims, 3 Drawing Sheets

ANTIFUNGAL COMPOSITION

Prevention of mould growth is an important topic to the food industry. Fungal spoilage can lead to considerable economic losses. Further, some mould species that contaminate food products, such as cheese, can produce mycotoxins which can penetrate into the food product (Scott, P.M.; "Mycotoxigenetic fungal contaminants of cheese and other dairy products" Mycotoxins in dairy products, Elsevier Science Publishers LTD, 193–259 (1989)). Therefore, removal of visible mould from a food product gives no guarantee of safety to the consumer.

For more than 30 years natamycin has been used to prevent fungal growth on cheeses and sausages.

Natamycin can be added to an emulsion of a polymer in water, mostly polyvinyl acetate, which is applied as a cheese coating (Daamen, C. B. G. and Berg, G van den; "Prevention of mould growth on cheese by means of natamycin" Voedingsmiddelentechnologie, 18 (2), 26–29 (1985)). Cheeses can also be treated by immersion in a suspension of natamycin in water (Morris, H. A. and Castberg, H. B.; "Control of surface growth on blue cheese using pimaricin" Cultured Dairy Products Journal, 15 (2), 21–23 (1980)). Sausages, however, are mainly treated by immersion or by spraying with a suspension of natamycin in water (Holley, R. A.; "Prevention of surface mold growth on Italian dry sausage by natamycin and potassium sorbate" Applied and Environmental Microbiology, 41 (2), 422–429 (1981)). Usually polymer emulsions for coating purposes contain 0.01 to 0.05% (w/v) of natamycin, while aqueous suspensions for immersion treatments contain 0.1 to 0.2% (w/v) of natamycin.

These treatments are generally effective in preventing fungal spoilage. However, fungal spoilage of products such as cheeses and sausages treated by dipping or spraying with an aqueous suspension of natamycin can still occur (Holley cited previously and Moerman, P. C.; "Schimmelwering op vleeswaren door Pimaricine" Voedingsmiddelentechnologie, 3 (51/51), 261–64 (1972)). This may be caused by an inhomogeneous distribution of natamycin on the surface of the product.

Holley describes the use of the thickening agent hydroxypropylmethylcellulose (HPMC) to prevent drip-loss of sorbate and natamycin from salami surfaces. It was demonstrated that drip-loss was reduced when HPMC was used at a concentration of 1%. However HPMC is not a suitable thickening agent for use in spray coating or dipping methods using aqueous suspension because of the long drying time. Although dripping can be prevented using concentrations of HPMC of 1% or more, the drying time of a product treated with a composition comprising 1% or more of HPMC will be more than 2 days. This is unacceptable for most practical purposes as the products e.g. cheeses or sausages can not be handled (e.g. transported) before they are dry. Lower concentrations of HPMC (e.g. 1 or 2 g/l) produce no substantial increase in the amount of natamycin on the treated surface. The term dry used herein means "hand-dry" i.e. dry enough for the products to be handled without undue difficulty.

DESCRIPTION OF THE INVENTION

The present inventors have found that a product treated with an aqueous composition comprising one or more suitable thickening agents in general in concentrations of 1 to 5 g/l, preferably 1 to 3 g/l, by dipping or spraying was dry within 5 hours. A drying time of 5 hours is acceptable for cheese and comparable with the drying time when dipping or spraying suspensions are used which do not contain a thickening agent.

The present invention relates to improved compositions of polyene fungicides, such as natamycin, which are suitable for the surface treatment of products especially natural products and particularly food products such as cheeses and sausages. These compositions may be used in a variety of applications including treatment of products by dipping and spraying.

Unexpectedly it has been found that mould growth on the surface of products is markedly reduced when they are treated with a composition wherein a suitable thickening agent is added to the aqueous dipping or spraying suspensions of polyene antifungal agents. Preferred compositions when applied to the product to be preserved, are capable of being dry at 20° C. within 5 hours at a relative humidity of 80%. The compositions also preferably give rise to an increase in the amount of natamycin on the surface of the product to be preserved of at least 30%, preferably at least 100%, when compared with the amount of natamycin present on the surface of the product in the case where a composition not comprising the suitable thickening agent is used.

The present inventors have found that the insufficient protection against fungal growth following dipping or spraying treatment with an aqueous suspension of a polyene antibiotic may be caused by the fat content of the product to be treated. The distribution of polyene fungicides, such as natamycin on surfaces containing a high amount of fat has been found to be inhomogeneous. The inhomogeneous distribution of the polyene fungicide is the consequence of the presence of fat particles at the surface of the products. When natamycin is added to the product via for example a coating, such as polyvinyl acetate, the distribution of the polyene fungicide will normally be homogeneous enough to prevent fungal infection. However, when products, for example cheeses or sausages, are treated by spraying or dipping methods using an aqueous composition, this will not always be the case. We have surprisingly found that the inclusion of the suitable thickening agent in the polyene antifungal composition leads to an increase in the degree of homogeneousness of the distribution of the polyene antifungal compound over the surface of the product. Also, the adhesion and the amount of natamycin to the surface of the food product is improved.

An improvement in the adhesion of the polyene fungicide may be of interest in the case of pre-soaking of casings used in the production of sausages. The pre-soaking of casings, which are generally protein-based or cellulose-based casings, in a conventional composition of natamycin is not a generally effective method of preventing fungal growth on the sausages (Holley & Moerman). The absorption of natamycin into the casings may not be optimal. Also, after coating of the sausages with the casing the sausages are usually washed by spraying with water. During this washing step part of the natamycin is washed from the sausages.

According to one aspect the invention provides a dry antifungal composition wherein the active component is a polyene antifungal compound (polyene fungicide), such as natamycin, and wherein a suitable thickening agent is added. Preferably the dry composition is an anhydrous composition most preferably a powder composition.

In a further aspect the invention provides an aqueous composition which may be a suspension. The aqueous composition may be prepared by dissolving the powder composition in a sufficient amount of water or by adding the polyene fungicide and the thickening agent separately. The invention also provides the use of the antifungal compositions of the invention for the treatment of natural products in particular food products such as cheeses and sausages including the pre-treatment of coatings such as casings for sausages and agricultural products such as fruit, grain, seed-potato, vegetables, flower bulbs, seed or feed products. The invention also provides the use of the compositions in pharmaceutical applications, in particular for applications which involve topical use of the composition. Examples of suitable pharmaceutical preparations are lotions, creams, ointments and shampoos.

The polyene antifungal compounds used in the compositions of the invention are preferably one or more of natamycin, nystatin, lucensomycin or amphotericin B. The preferred polyene compound is natamycin. In the preparation of compositions of the invention, one or more polyene antifungal compounds may be used or pre-prepared compositions containing such antifungal components may be used. An example of such a preparation is the commercially available powder composition sold under the trade mark Delvocid® which contains 50% (w/w) natamycin.

The concentration of polyene fungicide in the aqueous suspension will generally be from 0.1 to 20 g/l, more preferably from 0.5 to 8 g/l and most preferably from 1 to 5 g/l.

In compositions of the invention the preferred thickening agents include all thickening agents known in the art for use in food products except HPMC, preferably the thickening agents are gums, more preferably xanthan gum and/or gellan gum.

The one or more thickening agents in the aqueous composition are preferably present in an amount of 0.5 to 50 g/l, more preferably from 0.5 to 20 g/l and most preferably from 1 to 3 g/l.

In a preferred embodiment the composition of the invention further comprises a salt, preferably a metal halide salt e.g. sodium chloride or potassium chloride. Sodium chloride is most preferred as salt. The salt is preferably present in an amount of 10–250 g/l, more preferably 50–200 g/l, most preferably 50–100 g/l. When the composition is aqueous the salt improves the drying properties of the composition on the product. Salt also prevents bacterial growth in the aqueous composition allowing it to be stored for a moderate time period. To prevent bacterial growth also any antibacterial agent which is known in the art may be included in the composition.

A suspending agent may be included in the composition. The suspending agent serves as a deflocculant. Suitable suspending agents are for example microcrystalline cellulose-sodium, carboxymethylcellulose (Avicel® RC), sodium dodecyl sulphate, polyethylene glycol, fumed silica, glycol and glycerol.

In some embodiments it has been found that no buffer is needed for the suspension. In general the pH of the suspension will be between 3–10, preferably the pH will be between 6–9, more preferably between 6.2–8.5 for the optimal natamycin addition and drying time.

An additional advantage of an aqueous suspension according to the invention is that the suspension is physically stable for at least 10 days without stirring.

A BRIEF DESCRIPTION OF THE DRAWINGS

The invention will now be described by way of example with reference to the accompanying Examples which should be regarded as non-limiting.

EXAMPLE 1

A dipping bath was made up using 5 g Delvocid®/l together with 80 g sodium chloride/l and several concentrations of xanthan gum (Keltrol® RD, Kelco International Limited) in the order from 1 to 4 g/l (pH=7.0).

Cheese blocks of young Gouda cheese (Fat content more than 50%), having dimensions 3*3*3 cm, were dipped in the solutions.

A minimum of 10 cheese blocks per trial were tested. The weight increase after dipping and the homogeneous distribution of the dipping solution on the block's were measured.

Figure 1:
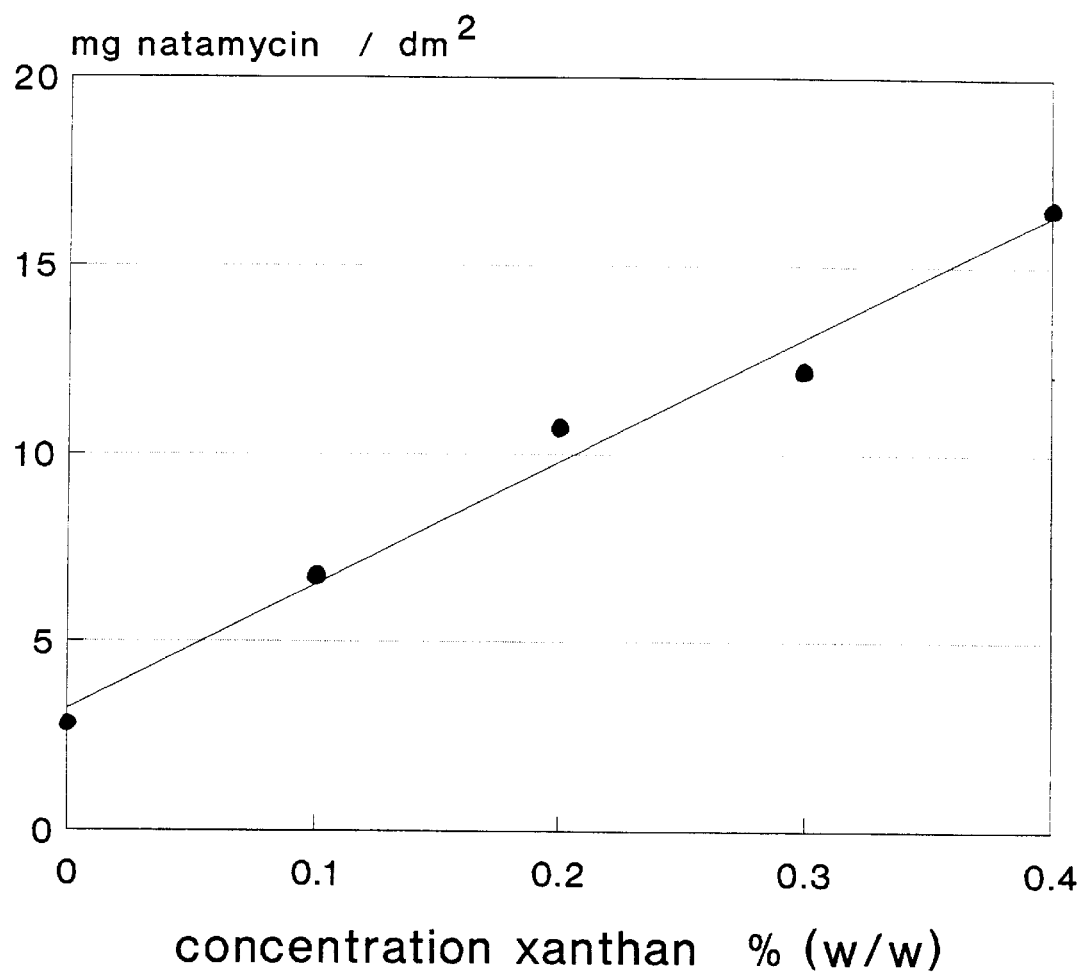
FIG. 1 shows the amount of natamycin on the final product as a function of the xanthan concentration in the dipping bath.

The dipping solution gave a linear increase in adhesion based on the concentration of xanthan gum from 2–3 mg natamycin/dm$^2$ to more than 10–15 mg natamycin/dm$^2$ (FIG. 1).

EXAMPLE 2

A dipping bath was made up using 5 g Delvocid®/l together with 0 or 4 g/l of xanthan gum (Keltrol® RD, Kelco International Limited).

Italico cheeses, cylinder type cheeses having an area of 11.3 dm$^2$ and a weight of 1.8 kg, were dipped in the described suspensions and the amount of dipping solution used was measured after dipping 10 cheeses.

Figure 2:
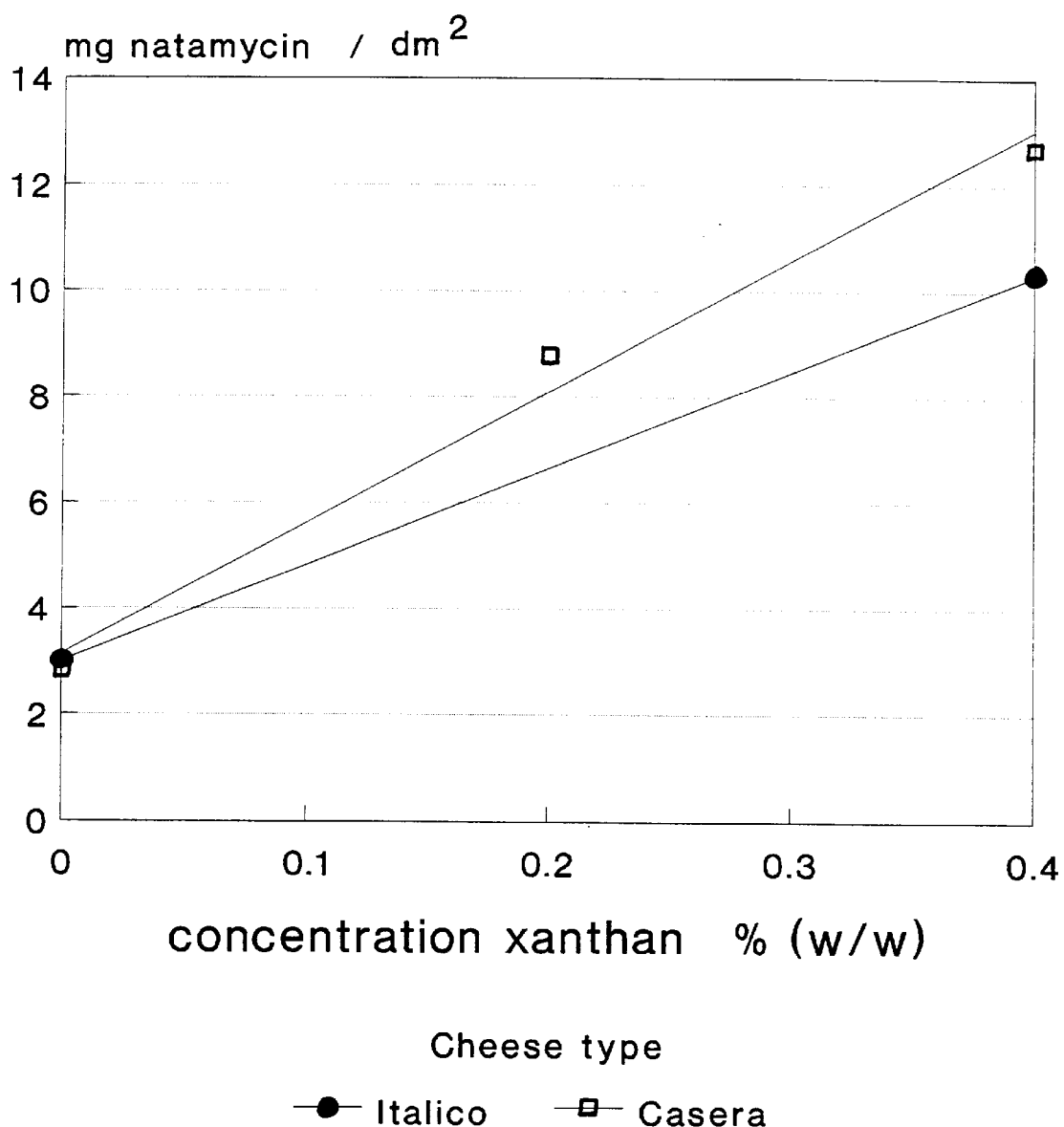
FIG. 2 shows the adhesion of natamycin on two types of cheese as a function of the xanthan concentration in the dipping bath.

The initial concentration of natamycin on the cheese was respectively 3 and 10.3 mg/dm$^2$, also shown in FIG. 2.

EXAMPLE 3

A dipping bath was made up using 5 g Delvocid®/l together with 0, 2 and 4 g/l of xanthan gum (Keltrol® RD, Kelco International Limited).

Casera cheeses, cylinder type cheeses having an area of 30.8 dm$^2$ and a weight of 8 kg, were dipped in the described suspensions and the amount of used dipping solution is measured after dipping 10 cheeses. The initial concentration of natamycin on the cheese was respectively 2.8, 8.8 and 12.7 mg/dm$^2$ (FIG. 2).

EXAMPLE 4

A dipping bath was made up using 5 g Delvocid®/l together with several concentrations of xanthan and 0 and 80 g/l sodium-chloride.

Gouda cheeses directly, after brining, were cut into blocks of dimensions 10*10*7 cm and dipped in the described dipping suspensions.

The blocks were incubated at a relative humidity of 81% and a temperature of 6° C.

Figure 3:
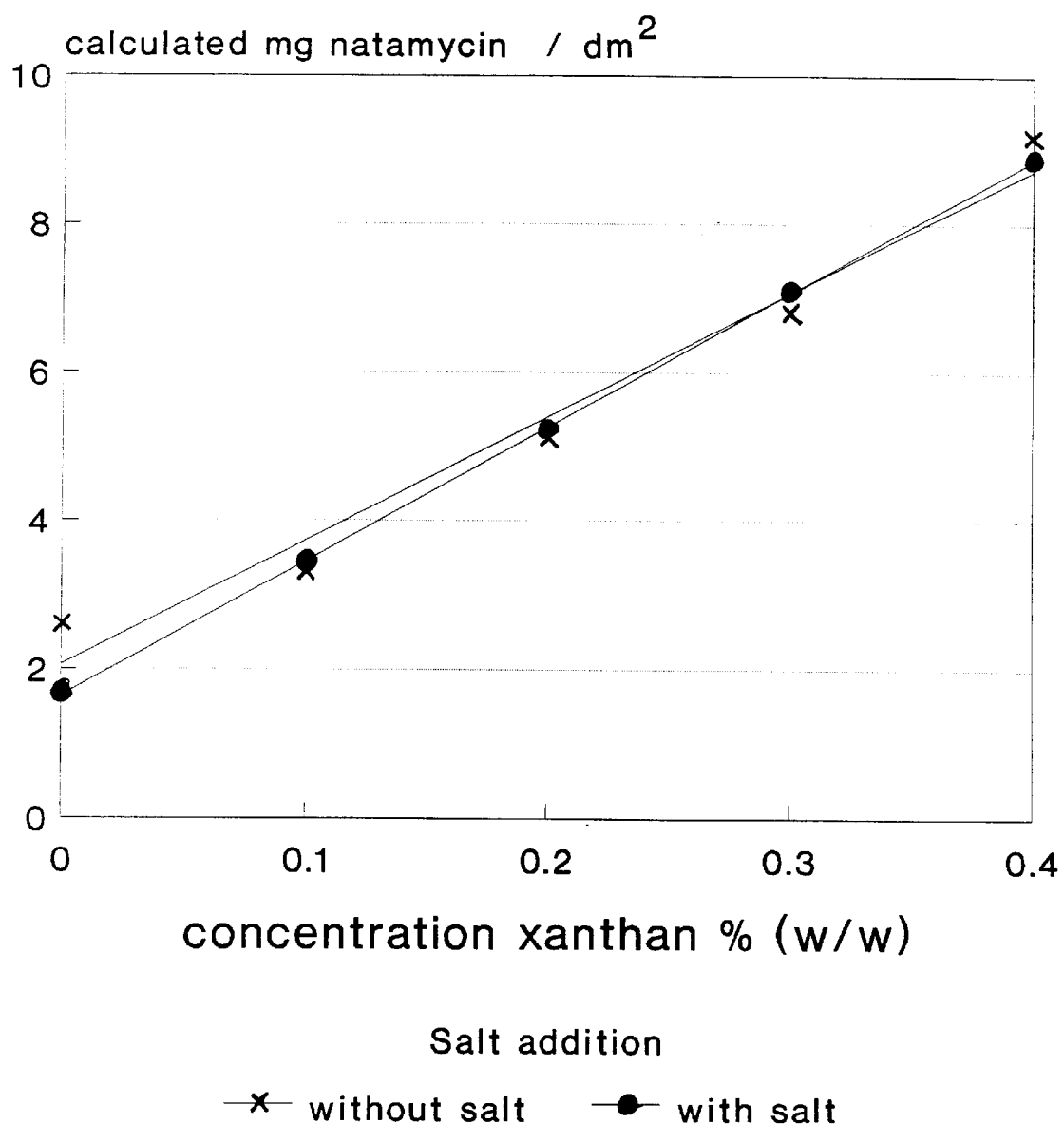
FIG. 3 shows the effect of salt addition to the dipping bath whereby the adhesion of natamycin to cheese is plotted as a function of the xanthan concentration in the dipping bath.

The used salt has no influence on the amount of natamycin adhered to cheese surface (FIG. 3).

Salt has a great influence on the drying behaviour of the dipped cheese blocks.

Using high concentration of xanthan (>than 3 g/l) or use a dipping solution without salt gives an unacceptable drying time of the cheese (more than two days).

The results are listed in detail in table 1.

The results are shown in table 1 and give a good impression of the influence of xanthan, salt and cheese side used.

| No° | Conc. Xant. (g/l) | Conc.Salt (g/l) | Drying time (hrs) on Cheese side | |
|---|---|---|---|---|
| | | | Upper side | Bottom side |
| 1 | 0 | 0 | 2 | 2 |
| 2 | 1 | 0 | 4 | 4 |
| 3 | 2 | 0 | 21 | 8 |
| 4 | 3 | 0 | >72 | 72 |
| 5 | 4 | 0 | >144 | >144 |
| 6 | 0 | 80 | 2 | 2 |
| 7 | 1 | 80 | 2 | 2 |
| 8 | 2 | 80 | 4 | 4 |
| 9 | 3 | 80 | 4 | 4 |
| 10 | 4 | 80 | 48 | 48 |

EXAMPLE 5

Suspensions made according to example 3 were tested on sedimentation characteristics.

The sedimentation characteristics were checked visually by putting 1000 ml of the resulting suspension into a measuring cylinder of 1000 ml. Even after 10 days standing no phase separation was observed.

EXAMPLE 6

A dipping bath was made up using 5 g Delvocid®/l together with 0 and 2 g/l xanthan and 80 g/l sodium-chloride.

Casera cheeses, treated with the two suspensions, were followed over time whilst observing the degree of mould development.

The ripening time usually used for these cheeses is 90 days at 5° to 8° C. in a warehouse with a relative humidity of 80 to 85%.

The results of the trial are shown in table 2.

TABLE 2

Extent of mould growth on the surface of the cheeses

| Time (days) | Normal treatment | Treatment with polymer |
|---|---|---|
| 40 | Cheese with moulds | No visible moulds |
| 70 | Total covered with mould | No visible moulds |
| 90 | Total covered with mould | No visible moulds |

EXAMPLE 7

A dipping bath was made up using 5 g Delvocid®/l together with 0 and 2 g/l xanthan and 80 g/l sodium-chloride.

Italico cheeses, treated with the two suspensions, were followed in time on mould development.

The ripening time usually used for these cheeses is 30–40 days at 5° C. in a warehouse with a relative humidity of 80%.

The results of the trial are shown in table 3.

TABLE 3

Extent of mould growth on the surface of the cheeses

| Time (days) | Normal treatment | Treatment with polymer |
|---|---|---|
| 40 | Traces of moulds | No visible moulds |
| 60 | Total covered with mould | No visible moulds |

EXAMPLE 8

Several dipping baths with different concentrations of natamycin and xanthum gum (Keltrol®, Kelco International Limited) are prepared. All dipping baths contain 12% (w/w) sodium chloride. Sausages with fibrous casing, are dipped in the solutions. Two sausages were tested per solution. The resulting natamycin concentration on the sausages are given in the table below.

| Concentrations of components (g/l) | | Natamycin on casing |
|---|---|---|
| Natamycin | Xanthan | (mg/dm$^2$) |
| 1.5 | 2.0 | 0.32 |
| 3.0 | 2.0 | 0.80 |
| 4.5 | 2.0 | 1.43 |
| 1.5 | 2.0 | 0.32 |
| 1.5 | 3.0 | 0.55 |
| 1.5 | 4.0 | 0.93 |

The results show that the natamycin concentration on the sausage increases proportionally with increasing natamycin concentration in the dipping solution. The natamycin concentration on the sausage increases more than proportionally with increasing xanthan gum concentration in the dipping solution.

EXAMPLE 9

Dipping baths with 1.0 g/l of natamycin, 2.0 g/l xanthan gum (Keltrol®, Kelco International Limited) and different concentrations of sodium chloride are prepared. Sausages with fibrous casings are dipped in the solutions. Two sausages were dipped per solution and the drying times of the coatings have been determined. The resulting natamycin concentration and drying time on the sausages are given in the table below.

| NaCl-concentration (g/l) | Drying time (hours) |
|---|---|
| 0.0 | 10 |
| 60.0 | 4 |
| 120.0 | 3 |

The results show that the drying time of the sausage decrease with increasing sodium chloride concentration in the dipping solution.

We claim:

1. An antifungal composition comprising one or more polyene antifungal compounds, one or more thickening agents and a salt selected from the group consisting of sodium chloride and potassium chloride, whereby none of the thickening agents is hydroxypropyl-methyl cellulose (HPMC), wherein the total amount of polyene antifungal compounds is 0.1 to 20 g/l and the total amount of thickening agent is 0.5 to 50 g/l and the salt is in an amount of 250 g/l.

2. A composition according to claim 1 wherein the weight ratio of the total amount of the polyene antifungal compounds to the total amount of the thickening agents is 1:500 to 40:1.

3. A composition according to any one of claims 1 to 2 which is an anhydrous composition.

4. A composition according to anyone of claims 1 to 2 which is an aqueous composition.

5. A composition according to claim 4 having a pH of between 6–9.

6. A composition according to claim 4 characterized in that it is capable of drying when located on the surface of a substrate treated with the composition for antifungal treatment in less than five hours when the temperature is maintained at 20° C. and relative humidity is maintained at 80%.

7. A composition according to claim 3 which, when added to water, results in a composition as defined in claim 5.

8. A composition according to claim 4 which is a sprayable composition.

9. A preventative antifungal treatment for nature products comprising contacting the natural product with the composition of claim 1.

10. An antifungal treatment which comprises either dipping a substrate to be treated or spraying a surface of a substrate with a composition according to claim 1.

11. A method for preventing fungal infection of a natural product with a composition as claimed in claim 1.

12. A natural product which has been treated with or has a coating of, a composition as claimed in claim 1.

13. A product according to claim 12 which comprises a foodstuff selected from cheese or sausage.

\* \* \* \* \*

UNITED STATES PATENT AND TRADEMARK OFFICE
CERTIFICATE OF CORRECTION

PATENT NO. : 5,962,510
DATED : October 5, 1999
INVENTOR(S) : De Haan and Ben Rudolf It is certified that error appears in the above-identified patent and that said Letters Patent is hereby corrected as shown below:

<u>Column 7, claim 1</u>,
Please delete "and the salt is in an amount of 250 g/l" and insert -- and the salt is in an amount of 20-250 g/l --

Signed and Sealed this

Second Day of April, 2002

Attest:

JAMES E. ROGAN
Attesting Officer   Director of the United States Patent and Trademark Office